United States Patent
Tonks

(10) Patent No.: US 6,479,640 B2
(45) Date of Patent: Nov. 12, 2002

(54) ANTIBODY SPECIFIC FOR A PROTEIN TYROSINE PHOSPHATASE THAT LOCALIZES TO FOCAL ADHESIONS

(75) Inventor: Nicholas K. Tonks, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/848,294

(22) Filed: May 3, 2001

(65) Prior Publication Data

US 2002/0049179 A1 Apr. 25, 2002

Related U.S. Application Data

(63) Continuation of application No. 09/235,251, filed on Jan. 22, 1999, now abandoned, which is a continuation of application No. 08/759,536, filed on Dec. 4, 1996, now Pat. No. 5,863,781, which is a division of application No. 08/107,420, filed on Aug. 16, 1993, now Pat. No. 5,595,911, which is a continuation of application No. 07/663,579, filed on Mar. 1, 1991, now abandoned, which is a continuation-in-part of application No. 07/494,036, filed on Mar. 14, 1990, now abandoned.

(51) Int. Cl.[7] .................. C07K 16/00; C07K 16/18; C07K 16/40
(52) U.S. Cl. .................. 530/388.26; 530/387.1; 530/387.7; 530/387.9; 530/388.1; 530/388.2
(58) Field of Search .................. 530/387.1, 387.9, 530/387.7, 388.1, 388.2, 388.26

(56) References Cited

U.S. PATENT DOCUMENTS

| 5,595,911 A | 1/1997 | Tonks |
| 5,604,094 A | 2/1997 | Schlessinger |
| 5,863,781 A | 1/1999 | Tonks |

FOREIGN PATENT DOCUMENTS

WO   WO 91/05568   *   5/1991

OTHER PUBLICATIONS

Bost et al. (Immunol. Invest. 1988; 17:577–586).*
Bendayan (J. Histochem. Cytochem. 1995; 43: 881–886).*
Lederman et al. (Molecular Immunology 28: 1171–1181, 1991).*
Li et al. (PNAS 77: 3211–3214, 1980).*
Rees, D.J.G. et al., "Sequence and Domain Structure of Talin", *Nature*, 347:685–689 (1990).
Tonks, N.K. et al., "Demonstration that Leukocyte Common Antigen CD45 is a Protein Tyrosine Phosphatase", *Biochemistry*, 27:8695–8701 (1988).
Streuli, M. et al., "Distinct functional roles of the two intracellular phosphatase like domains of the receptor–linked protein tyrosine phosphatases LCA and LAR", *The EMBO Journal*, 9:2399–2407 (1990).

Cool et al., "cDNA isolated from a human T–cell library encodes a member of the protein–tyrosine–phosphatase family", *PNAS*, vol. 86, pp. 5257–5261, Jul. 1989.
Charbonneau et al., "Human placenta protein–tyrosine–phosphatase: amino acid sequence and relationship to a family of receptor–like proteins", *PNAS*, vol. 86, pp. 5252–5256, Jul. 1989.
Charbonneau et al., "The leukocyte common antigen (CD45): a putative receptor–linked protein tyrosine phosphatase", *PNAS*, vol. 85, pp. 7182–7186, Oct. 1988.
Suggs et al., "Use of synthetic oligonucleotides as hybridization probes:isolation of cloned cDNA sequences for human beta 2–microglobulin", *PNAS*, vol. 78, No. 11, pp. 6613–6617, Nov. 1981.
Reeck, et al., "'Homology' in proteins and nucleic acids:a terminology muddle and a way out of it", *Cell*, vol. 50, 667 Aug. 28, 1987.
Zhang et al., "Biochemical Characterization of a Human Band 4.1–related Protein–tyrosine Phosphatase, PTPH1 (*)", *JBC Online, Life and Medical Sciences Online*, vol. 270 (34):20067–20072, (Aug. 1995).
Zhang et al., "Identification of the Cell Cycle Regulator VCP (p97/CDC48) as a Substrate of the Band 4.1–related Protein–tyrosine Phosphatase PTHP1*", *The Journal of Biological Chemistry*, vol. 274 (25) :17806–17812, (Jun. 1999).
S. Han et al., "Cytoskeletal protein tyrosine phosphatase PTPH1 reduces T cell antigen receptor signaling", *European Journal of Immunology*, vol. 30 (5) :1318–1325, (May 2000).
Zhang et al., "Serine Phosphorylation–dependent Association of the Band 4.1–related Protein–tyrosine Phosphatase PTPH1 with 14–3–3β Protein*", *The Journal of Biological Chemistry*, vol. 272 (43) :27281–27287, (Oct. 1997).
Verma, I.M. et al., "Gene therapy–promises, problems and prospects", *Nature*, vol. 389, pp. 239–242, (Sep. 1997).
Mulligan, R.C., "The Basic Science of Gene Therapy", *Science*, vol. 260, pp. 926–931, (May 1993).
Peng, K–W et al., "Vector development for cancer gene therapy", *Tumor Targeting*, 4., pp. 3–11, (1999).

(List continued on next page.)

Primary Examiner—Phillip Gambel
Assistant Examiner—Jessica H. Roark
(74) *Attorney, Agent, or Firm*—Hamilton, Brook, Smith & Reynolds, P.C.

(57) ABSTRACT

An antibody is provided that is specific for a PTPH1 protein, a phosphatase that dephosphorylates phosphotyrosine residues in phosphoproteins having tyrosyl residues that are phosphorylated by tyrosine kinases. The PTPH1 protein localizes to focal adhesions, a major site of action for oncogenic protein tyrosine kinases. PTPH1 overexpression may counter the effects of oncogenic protein tyrosine kinases, such as those of transforming viruses, by interfering with or reversing cell transformation that is associated with the activity of a protein tyrosine kinase.

3 Claims, 6 Drawing Sheets

OTHER PUBLICATIONS

Ledley, F.D., "Pharmaceutical Approach to Somatic Gene Therapy", *Pharmaceutical Research,* vol. 13, pp. 1595–1614, (Nov. 1996).

Tonks, N.K. et al., "From Form to Function:Signaling by Protein Tyrosine Phosphatases", *Cell,* vol. 87, pp. 365–368, (Nov. 1996).

Flint, A.J., et al, "Development of "substrate–trapping" mutants to identify physiological substrates of protein tyrosine phosphatases", *Proc. Natl. Acad. Sci.,* vol. 94, pp. 1680–1685, (Mar. 1997).

Neel, B.G. et al., "Protein tyrosine phosphatases in signal transduction", *Current Opinion in Cell Biology,* vol. 9, pp. 193–204.

Arimura, Y. et al.,GenCore Accession No. S39392, pp. 4–5, (May 1993).

Watson, J.D. et al., "Recombinant DNA", *Scientific American Books,* Second Edition, ( W.H. Freeman and Company, New York), Chapter 12, pp. 224–227; 1992.

\* cited by examiner

| | |
|---|---|
| PTPH1 | ICSIHFLDGVVQTFKVTKQDTGQVLLDMVHNHLGVTEKEYFGLQHDDDSVDSPRWLEA |
| Human 4.1 | HCKVSLLDDTVYECVVEKHAKGQDLLKRVCEHLNLLEEDYFGLAIWDNA-TSKTWLDS |
| Human ezrin | INVRVTTMDAELEFAIQPNTTGKQLFDQVVKTIGLREVWYFGLHYVDNK-GFPTWLKL |
| Mouse talin | GITNHDEYSLVRELMEEKKDEGTGTLRKDKTLL-RDEKKMEKLKQKLHTDDELNWLDH |
| | |
| PTPH1 | SKPIRKQLKGGF-PCTLHFRVRFFIPDPNTLQQEQTRH-LYFLQLKMDICEGRLTCPL |
| Human 4.1 | AKEIKKQVRGV--PWNFTFNVKFYPPDPAQLTEDITRYYL-CLQLRQDIVAGRLPCSF |
| Human ezrin | DKKVSAQEVRKENPLQFKFRAKFYPEDVAEELIQDITQKLFFLQVKEGILSDEIYCPP |
| Mouse talin | GRTLREQGVEE--HETLLLRRKFFYSDQNVDSRDPVQLNLLYVQARDDILNGSHPVSF |
| | |
| PTPH1 | NSAVVLASYAVQSHFGDYNSSIHHPGYLSDSHFIPDQ-------NEDFLTKVESLHE |
| Human 4.1 | ATLALLGSYTIQSELGDYDPELHGVDYVSDFKLAPNQ-------TKELEEKVMELHK |
| Human ezrin | ETAVLLGSYAVQAKFGDYNKEVHKSGYLSSERLIPQRVMDQHKLTRDQWEDRIQVWHA |
| Mouse talin | DKACEFAGFQCQIQFGPHNEQKHKAGFLDLKDFLPKE------YVKQKGERKIFQAHK |
| | |
| PTPH1 | QHSGLKQSEAESCYINIARTLDFYGVELHSGRDLHNLDLMIGIASAGVAVYRK----- |
| Human 4.1 | SYRSMTPAQADLEFLENAKKLSMYGVDLHKAKDLEGVDIILGVCSSGLLVYKD----- |
| Human ezrin | EHRGMLKDNAMLEYLKIAQDLEMYGINYFEIKNKKGTDLWLGVDALGLNIYEK--DDK |
| Mouse talin | NCGQMSEIEAKVRYVKLARSLKTYGVSFFLVKEKMKGKNKLVPRLLGITKECVMRVDE |
| | |
| PTPH1 | YICTSFYPWVNI--LKISFKRKKFFIHQRQKQAESREHIVAFNMLNYRSCKNLWKSCV |
| Human 4.1 | KLRINRFPWPKV--LKISYKRSSFFIKIRPGEQEQYESTIGFKLPSYRAAKKLWKVCV |
| Human ezrin | LTPKIGFPWSEI--RNISFNDKKFVIKPIDKKAPDFV----FYAPRLRINKRILQLCM |
| Mouse talin | KTKEVIQEWSLTNIKRWAASPKSFTLDFGDYQDGYYSVQTTEGEQIAQLIAGYIDIIL |
| | |
| PTPH1 | EHHTFFQAKKLLPQEKNVLSQYWTMGSRNTKKSVNNQYCKKVIGMVWNPAMRRS |
| Human 4.1 | EHHTTF---RLTSTDTIPKSKFLALGSK-FRYSGRTQAQTRQASALIDRPAPHFE |
| Human ezrin | GNHELYMRRRKPDTIEVQQMKAQAREEKHQKQLERQQLETEKKRRETVEREKEQM |
| Mouse talin | KKKKSKDHFGLEGDEESTMLEDSVSPKKSTVLQQQYNRVGKVEHGSVALPAIMRS |

FIGURE 4A

```
PTPH1           NLDKNRYKDVLPYDTTRVLLQGN----------------------------------EDYINASYVNM
PTPase 1B       NKNRNRYRDVSPFDHSRIKLHQED----------------------------------NDYINASLIKM
T-Cell PTPase   NRNRNRYRDVSPYDHSRVKLQNAE----------------------------------NDYINASLVDI
Human CD45 D1   NQNKNRYVDILPYDYNRVELSEINGDAG------------------------------SNYINASYIDG
Human CD45 D2   NKSKNRNSNVIPYDYNRVPLKHELEMSKESEHDSDESSDDDSDSEEPSKYINASFIMS PTPH1           EIPAANLVNKYIATQGPLPHTCAQFWQVWDQKLSLIVMLTTLTERGRTKCHQYWP--
PTPase 1B       EEAQR----SYILTQGPLPNTCGHFWEMVWEQKSRGVVMLNRVMEKGSLKCAQYWPQK
T-Cell PTPase   EEAQR----SYILTQGPLPNTCCHFWLMVWQQKTKAVVMLNRIVEKESVKCAQYWP-T
Human CD45 D1   FKEPR----KYIAAQGPRDETVDDFWRMIWEQKATVIVMVTRCEEGNRNKCAEYWP--
Human CD45 D2   YWKPE----VMIAAQGPLKETIGDFWQMIFQRKVKVIVMLTELKHGDQEICAQYWG--

PTPH1           -DPPDVMNHGGFHIQCQSEDCTIAYVSREMLVTN-TQTGEEHTVTHLQYVAWPDHGIP
PTPase 1B       EEKEMIFEDTNLKLTLISEDIKSYYTVRQLELEN-LTTQETREILHFHYTTWPDFGVP
T-Cell PTPase   DDQEMLFKETGFSVKLLSEDVKSYYTVHLLQLEN-INSGETRTISHFHYTTWPDFGVP
Human CD45 D1   SMEEGTRAFGDVVVKINQHKRCPDYIIQKLNIVNKKEKATGREVTHIQFTSWPDHGVP
Human CD45 D2   ---EGKQTYGDIEVDLKDTDKSSTYTLRVFELRH-SKRKDSRTVYQYQYTNWSVEQLP PTPH1           DDSSDFLEFVNYVR-------------SLRVDSEPVLVHCSAGIGRTGVLVTMETAMCLT
PTPase 1B       ESPASFLNFLFKVR-------------ESGSLSPEHGPVVHCSAGIGRSGTFCLADTCLLM
T-Cell PTPase   ESPASFLNFLFKVR-------------ESGSLNPDHGPAVIHCSAGIGRSGTFSLVDTCLVM
Human CD45 D1   EDPHLLLKLRRRVN-------------AFSNFFSGPIVVHCSAGVGRTGTYIGIDAMLEGL
Human CD45 D2   AEPKELISMIQVVKQKLPQKNSSEGNKHHKSTPLLIHCRDGSQQTGIFCALLNLLESA PTPH1           ERNLP---IYPLDIVRKMRDQRAMMVQTSSQYKFVCEAILRVYEEGLVQMLDPS
PTPase 1B       DKRKDPSSVDIKKVLLEMRKFRMGLIQTADQLRFSYLAVIEGAKFIMGDSSVQD
T-Cell PTPase   EKGDD---INIKQVLLNMRKYRMGLIQTPDQLRFSYMAIIEGAKCIKGDSSIQK
Human CD45 D1   EAENK---VDVYGYVVKLRRQRCLMVQVEAQYILIHQALVEYNQRGETEVNLSE
Human CD45 D2   ETEEV---VDIFQVVKALRKARPGMVSTFEQYQFLYDVIASTYPAQNGQVKKNN
```

FIGURE 4B

ANTIBODY SPECIFIC FOR A PROTEIN TYROSINE PHOSPHATASE THAT LOCALIZES TO FOCAL ADHESIONS

RELATED APPLICATION

This application is a continuation of U.S. application Ser. No. 09/235,251, filed Jan. 22, 1999, now abandoned, which is a continuation of U.S. application Ser. No. 08/759,536, filed Dec. 4, 1996, now issued U.S. Pat. No. 5,863,781, which is a divisional of U.S. application Ser. No. 08/107,420, filed Aug. 16, 1993, now issued, U.S. Pat. No. 5,595,911, which is a file wrapper continuation of U.S. application Ser. No. 07/663,579, filed Mar. 1, 1991, now abandoned, which is a continuation-in-part of U.S. application Ser. No. 07/494,036, filed Mar. 14, 1990, now abandoned. The contents of all the above applications are incorporated herein by their entirety.

FUNDING

Work described herein was funded by Cold Spring Harbor Laboratory.

BACKGROUND

Focal adhesion plaques are specialized regions of the plasma membrane through which cells in culture adhere to the external substrate (Burridge, K. et al., *Ann Rev. Cell. Biol.*, 4:487–525 (1988); Burridge, K. and K. Fath, *BioEssays*, 10:104–108 (1989)). On their internal face these structures anchor actin stress fibers, which are important in determining cell shape. Similar, but less well-characterized structures have been implicated in attachment between neighboring cells and adherence to extracellular matrix in vivo. Oncogenic transformation is frequently accompanied by a less-adherent, rounded morphology resulting from reorganization of the cytoskeleton (Ben Ze'ev, A., *Biochem. Biophys. Acta.*, 780:197–212 (1985; Felice, G. R. et al., *Eur. J. Cell Biol.*, 52:47–49 (1990)). In Rous Sarcoma Virus (RSV) transformed cells, for instance, it has been postulated that a contributing factor is the aberrant phosphorylation by pp60$^{v-src}$ of tyrosyl residues in key focal adhesion proteins (Burr, J. G. et al., *Proc. Natl. Acad. Sci. USA*, 77:3484–3488 (1980); Parsons, J. T. and M. J. Weber, *Curr. Topics in Microbiol. and Immunol.*, 147:79–127 (1989)). Phosphotyrosine has also been detected in focal adhesions (Maher, P. A. et al., *Proc. Natl. Acad. Sci. USA*, 82:6576–6580 (1985)) and apical junctions (Takata, K. and S. J. Singer, *J. Cell Biol.*, 106:1757–1764 (1988)) in nontransformed cells, raising the possibility that tyrosine phosphorylation at these sites may regulate normal cellular function. Such phosphorylation events must be tightly controlled and an understanding of the mechanism(s) involved would be very useful in furthering our understanding of control of normal and neoplastic cell growth.

SUMMARY OF THE INVENTION

The present invention relates to DNA which encodes a protein homologous to the protein tyrosine phosphatases (PTPases) which catalyze the dephosphorylation of proteins in which tyrosyl residues have been phosphorylated through the action of a protein kinase. The protein, which appears as if it will localize to focal adhesions, is also the subject of the present invention. In particular, it relates to cDNA encoding a protein, referred to as PTPH1, which was obtained from HeLa cells and characterized. PTPH1 has also been identified in other cell types. The structure of PTPH1 includes three segments: 1) an N-terminal segment of approximately 320 residues, which shows homology with the N-terminal segments of the talin family in the region known to be important for localization to focal adhesions; 2) a central segment, in which there are sequences with the features of sites of phosphorylation by casein kinase 2 and p34$^{cdc2}$, which may be important for regulation of phosphatase activity; and 3) a C-terminal segment of approximately 250 residues, which shows homology to the known members of the PTPase family. PTPH1 has a single putative catalytic domain.

Because of its homology with the talin family of proteins, which are known to participate in linkage of intracellular actin filaments to the extracellular matrix at focal adhesions, it is likely that PTPH1 localizes to the focal adhesions, which is a major site ofaction. for oncogenic protein tyrosine kinases (PTK). Thus, overexpression of PTPH1 may be a powerful approach to countering the effects of oncogenic protein tyrosine kinases, such as those of transforming viruses, and interfering with or reversing cell transformation. This would provide a means of preventing or reversing abnormally high levels of phosphotyrosine associated with any disease or condition, such as preventing or reversing malignancy associated with the activity of a protein tyrosine kinase. Such protein tyrosine kinase may be of viral origin or be a cellular protein tyrosine kinase whose normal cellular function is disrupted, resulting in abnormal phosphorylation of tyrosyl residues. Such a method of preventing or reversing malignancy caused by or associated with the activity of a protein tyrosine kinase is also the subject of the present invention. In the present method, DNA or RNA encoding PTPH1 or a functional equivalent of PTPHl is administered to an individual in an appropriate gene transfer vehicle which can infect mammalian cells and, once inside the mammalian cells, express and make available PTPH1 or its functional equivalent in sufficient quantities to overcome or counteract the protein tyrosine kinase activity. As a result, phosphorylation of tyrosine residues at abnormal levels is prevented or reversed, resulting in turn in prevention or reversal of malignancy of cells. Suitable gene transfer vehicles are those which contain DNA or RNA encoding PTPH1 or a PTPH1 functional equivalent, can infect mammalian cells and express the encoded protein within the infected mammalian cells. Such vehicles include recombinant retroviruses and recombinant vaccinia virus.

The method of the present invention is useful in treating or preventing a wide variety of conditions in which abnormally high levels of phosphotyrosine occur and particularly in treating or preventing malignancies in which tyrosyl phosphorylation by a protein tyrosine kinase occurs at an abnormal rate or level and in which dephosphorylation of tyrosyl residues by PTPH1 or its functional equivalent results in prevention or reversal of a malignant phenotype.

BRIEF DESCRIPTION OF THE DRAWINGS

FIGS. 1A–1B shows the nucleotide sequence (SEQ ID NO:1) and the deduced amino acid sequence (SEQ ID NO:2) of PTPH1.

FIGS. 4A–4B shows the alignment of the amino acid residues of PTPH1 and the conserved domains in related proteins. FIG. 4A is a comparison of the sequence of the N-terminal segment PTPH1 (SEQ ID NO:3) with the homologous domain in band 4.1 (SEQ ID NO:4), ezrin (SEQ ID NO:5) and talin (SEQ ID NO:6). FIG. 4B is a comparison of the PTPase-like domain in PTPH1 (SEQ ID NO:7) with the catalytic domains of two low Mr. PTPases (PTP1B (SEQ ID NO:8) and TCPTP (SEQ ID NO: 9)) and a receptor linked form (CD45 (SEQ ID NOs: 10 and 11).

DETAILED DESCRIPTION OF THE INVENTION

Figure 2:
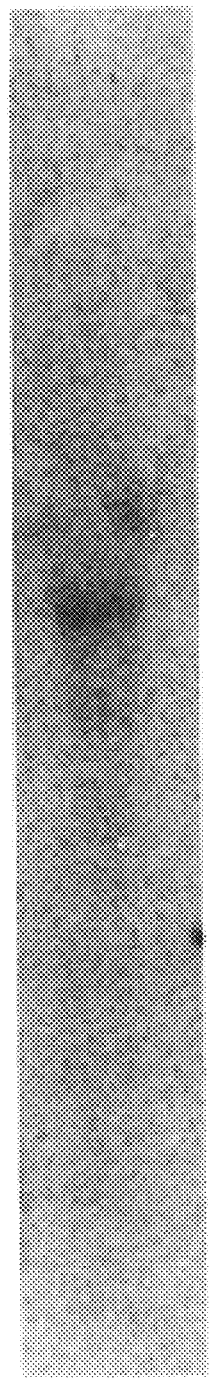
FIG. 2 shows the results of northern blot analysis of PTPH1 mRNA from HeLa cells.

The present invention relates to DNA encoding a protein tyrosine phosphatase which appears to localize to focal adhesions. In particular, it relates to PTPH1, which in one segment is homologous to the protein tyrosine phosphatases (PTPases) and in another segment is homologous to a family of proteins which are located at the interface between the plasma membrane and the cytoskeleton. The present invention also relates to the encoded PTPH1 protein, RNA encoding the PTPH1 protein, antibodies specific for PTPH1 protein and methods of using the DNA encoding PTPH1 and the PTPH1 protein. DNA encoding PTPH1 can be used to prevent or reverse phosphorylation of tyrosine residues in proteins which have been phosphorylated by a protein tyrosine kinase.

As described herein, a protein which is a homologue of the protein tyrosine phosphatases has been identified by means of amplification of PTPase-related cDNAs. In addition, the deduced amino acid sequence of PTPH1 has been compared with the amino acid sequences of other proteins with known activities. As a result, PTPH1 has been shown to have three segments. As described below, the characteristics of at least two of these regions make it reasonable to expect that PTPH1 localizes to the focal adhesions and has intrinsic phosphatase activity.

The following is a summary of aspects of cytoskeletal components and maintenance of cytoskeletal integrity and description of the identification of PTPH1. Also described are the possible role of PTPH1 in maintaining cytoskeletal integrity and preventing or reversing tyrosyl phosphorylation and a method of preventing or reversing malignant transformation of mammalian cells. In the method of preventing or reversing malignant transformation, DNA or RNA encoding PTPH1 or a PTPH1 functional equivalent is introduced into cells and expressed in sufficient quantities to prevent or reverse abnormal tyrosyl phosphorylation, resulting in prevention of transformation of the cells or reversal of the malignant phenotype.

The actin stress fibers are a component of the cytoskeleton that are important for the determination of cell shape and also for attachment to the substratum. These actin cables interact with the cell membrane at regions described as focal contacts, focal adhesions or adhesion plaques. Fibronectin is an extracellular glycoprotein that is arranged in immobilized fibrillar arrays across the surface of many cells, forming network that interconnects cells with each other. The receptors for fibronectin on the cell surface are termed integrins. Integrins are also localized to focal adhesions and provide the transmembrane link between components of the extracellular matrix, such as fibronectin and vitronectin, and the cytoskeleton.

Progress has been made in identifying the components of the focal adhesions that provide the link between the integrins and the actin fibers; however, the picture is not yet complete. At present it is thought that the integrins interact indirectly with actin cables through a multiprotein complex.

Talin interacts with the cytoplasmic segment of the integrin β chain and also binds to vinculin. Vinculin has been shown to interact with α actinin, which can bind actin directly. Of these components, vinculin, talin and the β subunit of the integrins are phosphorylated on tyrosyl residues. A correlation has yet to be established between such phosphorylation and the appearance of the transformed phenotype. However, this picture is undoubtedly imcomplete. Other substrates of tyrosine phosphorylation, including two focal adhesion associated proteins, paxillin and ezrin, have also been identified. Furthermore, microtubules and intermediate filaments may also terminate at focal adhesions but the nature of the proteins that facilitate this interaction is unknown. Thus, additional focal adhesion associated proteins remain to be characterized and their function established. Protein and cDNA sequence analysis has defined a family of proteins that include talin (Rees, D. J. G. et al., *Nature*, 347:685–689 (1990)), ezrin (Turunen, O. et al., *J. Biol. Chem.*, 264:16727–16732 (1989); Gould, K. L. et al., *EMBO J.*, 8:4133–4142 (1989)) and band 4.1, (Conboy, J. et al., *Proc. Natl. Acad. Sci. USA*, 83:9512–9516 (1986)) which participate in the interaction between the membrane and cytoskeleton. They possess a homologous N-terminal domain that appears to associate with protein components in the plasma membrane. In band 4.1, which promotes association of actin and spectrin in erythrocytes, this domain interacts with the transmembrane protein glycophorin (Bennett, V., *Biochem. Biophys. Acta.*, 988:107–121 (1989)). A similar model has been proposed for the interaction of talin with integrin (Rees, D. J. G. et al., *Nature*, 347:685–689 (1990)). In the case of ezrin, which displays a submembranous localization in brush border cells, the details of its interaction with other proteins remain to be established.

Identification of the complement of protein tyrosine phosphatases in HeLa cells was carried out as described in detail in Example 1. Briefly, protein tyrosine phosphatase-related cDNAs were amplified in the polymerase chain reaction (PCR) using primers corresponding to conserved segments within the catalytic domains. The PCR reaction products (approximately 0.25 kb) were subcloned into pUC118; of 77 independent subclones sequenced, 15 corresponded to a novel PTPase isoform termed PTPH1. A total of $4.2 \times 10^6$ phage plaques from the same HeLa cell cDNA library were probed with the PCR product and 10 positive clones were identified.

Figure 1A:
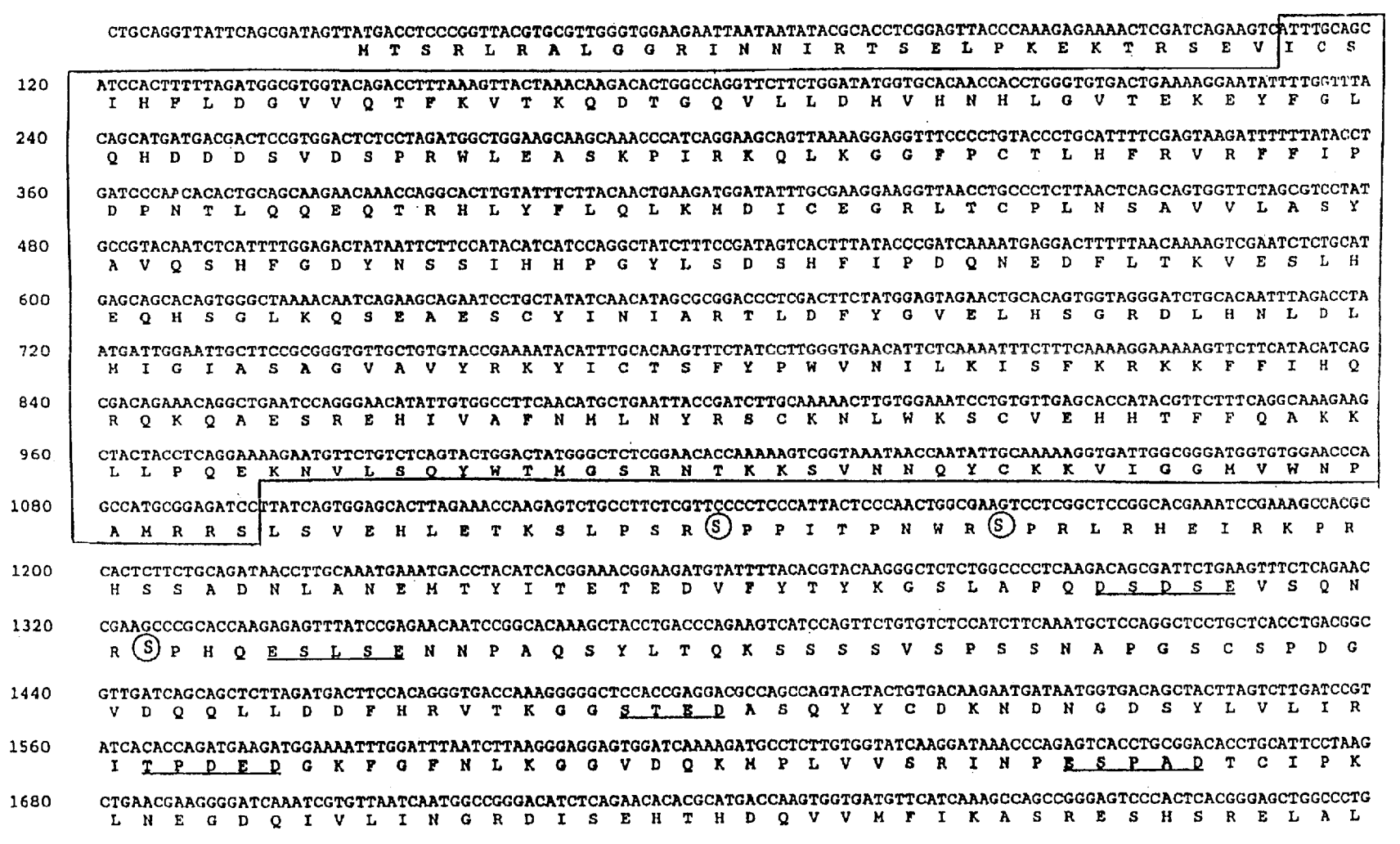
Figure 1B:
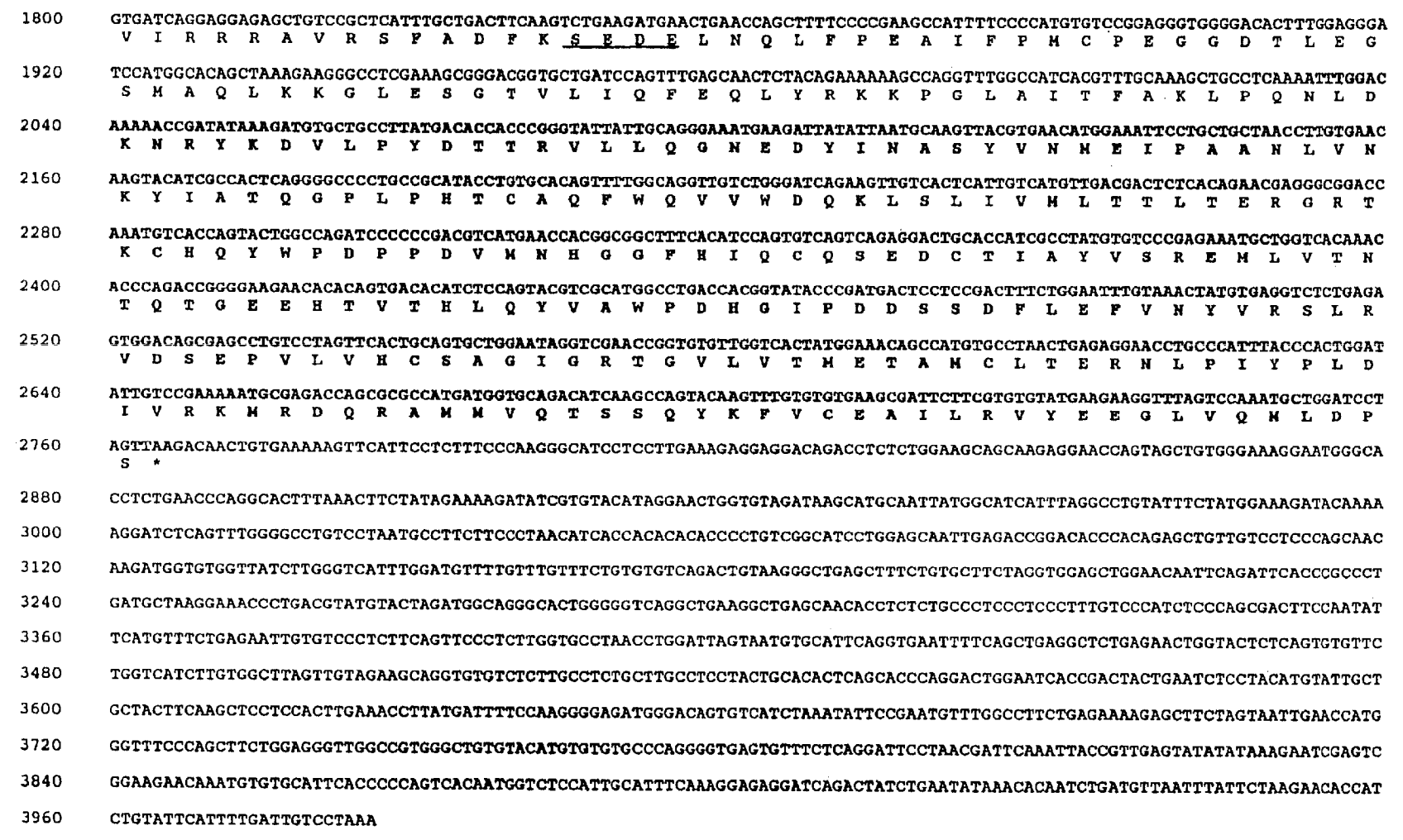

The sequence of the longest clone (3984 bp) is presented in FIG. 1. It has a 5'-noncoding segment of 23 bp followed by an open reading frame, from the first available ATG, of 2739 bp. This open reading frame would encode a protein of 913 amino acids with a predicted Mr of approximately 104 k. Although the sequence surrounding the putative initiator does not conform well to the Kozak consensus sequence (Kozak, M., *J. Cell. Biol.*, 108:229–241 (1989)), there is a purine at position −3 which is an important requirement for an initiation site. Furthermore, translation of RNA, synthesized from PTPH1 cDNA, in a reticulocyte lysate yielded a protein of approximately 120 kDa, close to the expected size. There is a 3' non-translated segment of 1222 bp, but the cDNA does not contain a consensus polyadenylation signal or a poly A tail. A transcript encoding PTPH1 was detected by northern blot analysis of HeLa cell polyA+ mRNA as a low abundance message of approximately 4.3 kb (FIG. 2). The slightly larger size of the mRNA may be explained in part by the absence of a poly A tail in the cDNA.

Figure 3:
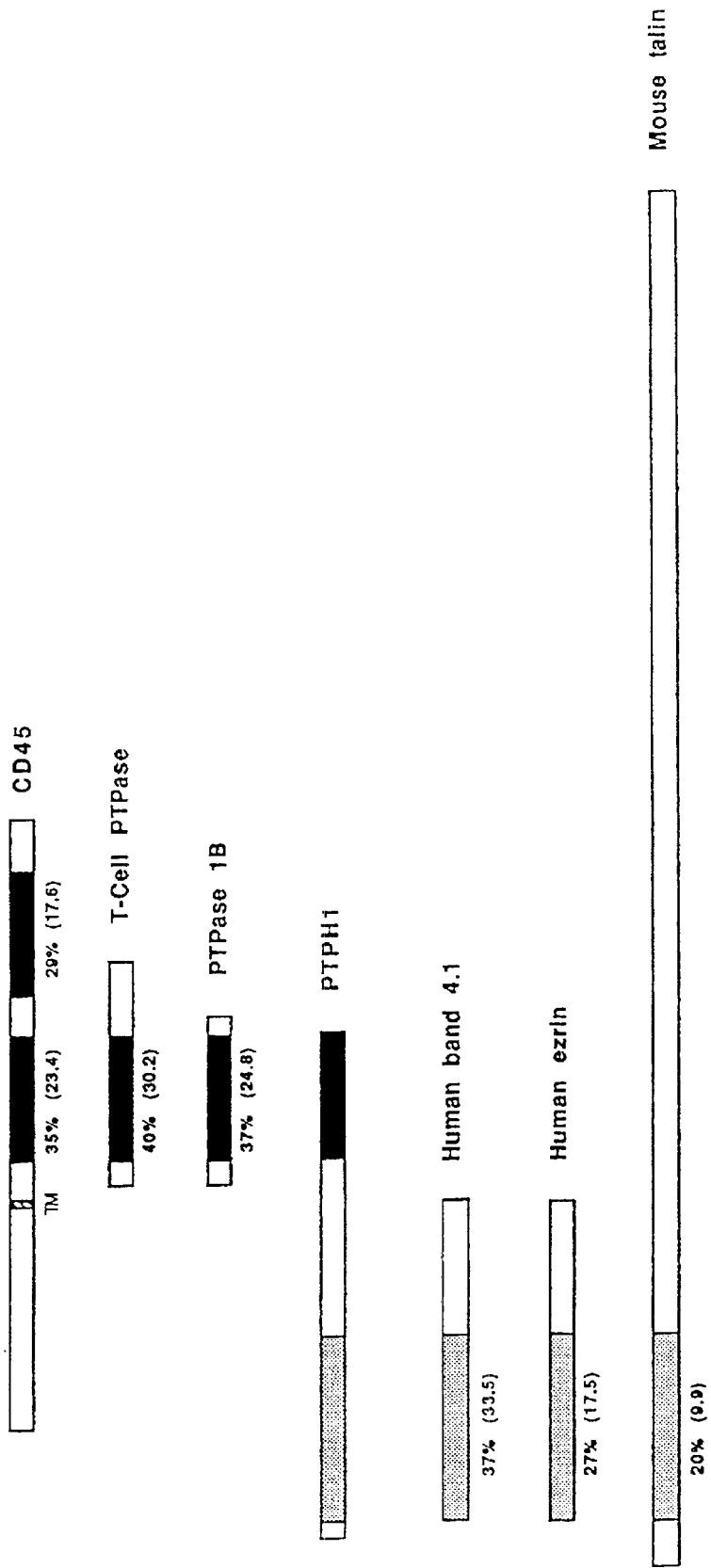
FIG. 3 is a schematic diagram illustrating the structure of PTPH1 and its relationship to CD45, T-cell PTPase and PTPase 1B and human band 4.1, human ezrin and mouse talin.

The sequence of PTPH1 can be described in terms of 3 segments, as summarized in FIG. 3. The alignment of amino acid residues of PTPH1 and the conserved domains in related proteins was also assessed. The results are represented in FIG. 4. In FIG. 4A, the sequence of the N-terminal segment of PTPH1 is compared with the homologous domain in 4.1, ezrin and talin. As shown in FIG. 4A, the N-terminal segment of PTPH1 is homologous to the domains in band 4.1, ezrin and talin that have been proposed to function in localizing these proteins to the interface between the plasma membrane and the cytoskeleton (Rees, D. J. G. et al., *Nature,* 347:685–689 (1990)), In FIG. 4B, the sequence of the protein tyrosine phosphatase-related domain of PTPH1 is compared with the catalytic domains of two low Mr PTPases (PTP1B and TCPTP) and a receptor-linked form (CD45). The C-terminal segment displays homology to the catalytic domain of the PTPases (FIG. 4B). As shown in FIG. 1, the central segment contains sequences that suggest potential phosphorylation sites for casein kinase II and p34$^{cdc2}$. While the dephosphorylation of tyrosyl residues in proteins by PTPH1 remains to be demonstrated, it should be noted that in CD45 (Tonks, N. K., et al., *Biochemistry,* 27:8695–8701 (1988))) and LAR (Sreuli, M et al., *EMBO J.,* 9:2399–2407 (1990)), which share comparable levels of sequence identity to PTP1B as displayed by PTPH1, intrinsic activity has been confirmed.

The PTPases comprise a rapidly expanding family of enzymes and it is anticipated that the various isoforms will have specific functions in vivo. The structure of PTPH1 may illustrate a general theme among the PTPases; within the protein, distinct structural motifs may, at least in part, control specificity by restricting intracellular localization. It is proposed that PTPH1 acts at the junction between the cytoskeleton and the plasma membrane and plays a role in controlling cytoskeletal integrity. The occurrence of a signal peptide sequence and a transmembrane domain in CD45 directs it to span the membrane. The C-terminal, non-catalytic segment of the low Mr, cytoplasmic PTPases also appears to direct association with the particulate fraction of cell extracts. In addition such structural motifs may determine how the activity of the catalytic domain is controlled. Thus for the receptor-like forms the binding of ligands to the extracellular segments may modulate activity. The C-terminal segment of the low Mr PTPase appears to repress the activity of the catalytic domain. If PTPH1 is localized to focal adhesions it should also be regulated to permit normal tyrosine phosphorylation at such sites in non-transformed cells. Phosphorylation of Ser/Thr residues in the central segment of the protein (FIG. 1) may directly modulate activity. In addition, by analogy with band 4.1 whose affinity for glycophorin is regulated by phosphatidylinositol-4,5-bisphosphate, it is possible that the localization of PTPH1 may alter with phosphatidylinositol turnover.

Considering the apparent correlation between RSV induced transformation and the cytoskeletal association of pp60$^{src}$ (Burr, J. G. et al., *Proc. Natl. acad. Sci. USA,* 77:3484–3488 (1980); Shriver, K. and L. R. Rohrschneider, *Cold Spring Harbor Conference Cell Proliferation,* 8:*Protein Phosphorylation,* 1247–1262 (1981); Hamaguchi, M. and Hanafusa, H., *Proc. Natl. Acad. Sci. USA,* 84:2312–2316 (1987); Tapley, P. et al., *Oncogene,* 4:325–333 (1989); Glenney, J. R., Jr. and Zokas, L., *J. Cell Biol.,* 108:2401–2408 (1989) PTPH1 is an excellent candidate PTPase with which to achieve a reversion of src-induced transformation and furthermore to delineate the precise role of tyrosine phosphorylation in the morphological changes induced by src. In addition, it clearly has potential to function as growth suppressor; the inactivation or deletion of the PTPH1 could conceivably in itself be sufficient to generate a transformed phenotype.

It has been known for some time that viral transformation, for instance by Rous Sarcoma Virus (RSV), brings about a decrease in cell adhesion that is associated with a rounding up of the cells, a reduction in the number of stress fibers and a loss of fibronectin-integrin association. In RSV transformed cells the number of focal adhesions is dramatically decreased and those that remain are altered in architecture. The transforming protein tyrosine kinase of RSV, pp60$^{v-src}$ is localized to the adhesion plaques; this is associated with an increased level of phosphotyrosine in these structures. In fact, the level of phosphotyrosine in the focal adhesions correlates with the density of actin stress fibers That is, the higher the level of phosphotyrosine, the less intact is the cytoskeleton. Therefore, it appears that the association of pp60$^{v-src}$ with the focal adhesions and the phosphorylation of tyrosyl residues in proteins within this structure are intimately involved in the disruption of the cytoskeleton.

Transforming genes, oncogenes, are mutated forms of normal cellular genes, termed proto-oncogenes. Malignant transformation can be described as a disruption of the normal modes of growth control, that is, transformed cells can divide in the absence of specific growth stimulatory factors or fail to respond to growth inhibitory signals. In other words, transformation may often result from the disruption of a normal cellular process. In this regard, it is interesting to note that in the normal process of mitosis, the cells round up and there is a transient disruption of focal contacts.

Antibodies to phosphotyrosine have indicated that tyrosine phosphorylation of focal adhesion (Maher, P. A. et al., *Proc. Natl. Acad. Sci. USA,* 82:6576–6580 (1985)) and apical junction (Takata, K. and S. J. Singer, *J. Cell Biol.,* 106:1757–1764 (1988)) proteins also occurs in non-transformed cells, suggesting the action of a PTK at these sites in normal cell function. However, the kinases involved have yet to be identified. In view of the potentially disastrous effects of aberrant tyrosine phosphorylation one would anticipate that the action of such PTKs would be tightly controlled. The localization of a PTPase to these structures is one means by which such regulation could be achieved.

The protein tyrosine phosphatases have been shown to constitute a family of both cytoplasmic, low-Mr and transmembrane receptor-linked forms. The work described herein has resulted in identification of a novel homologue of the protein tyrosine phosphatases in epithelial cells, specifically HeLa cells, which are a model system for the study of the cell cycle. As described, this protein tyrosine phosphatase (PTPH1) has homology with the talin family of proteins and, therefore, can be expected to localize to the interface between the plasma membrane and the cytoskeleton, such as at focal adhesions, which are a major site of action of oncogenic protein tyrosine kinases. Such a protein tyrosine phosphatase is referred to herein as one which localizes to the interface between the plasma membrane and the cytoskeleton. Overexpression of PTPH1 can be used to counter the effects of protein tyrosine kinases, such as v-src.

As a result of the findings described herein, a protein tyrosine phosphatase which appears to localize to focal adhesions, which is a major site of action for oncogenic protein tyrosine kinases is available, as are DNA and RNA encoding the protein. The ability of PTPH1 or a functional equivalent to reverse malignant transformation of cells can be assessed using known methods. For example, this can be carried out as follows: briefly, cells, for instance chicken embryo fibroblasts or NIH 3T3 cells, which are transformed by introduction of a viral oncogene such as v-src, display a change in morphology relative to the non-transformed controls. They will grow in soft agar and induce tumor formation in nude mice. Transformed cells are transfected with the PTPH1 DNA using an appropriate expression vector. The ability of PTPH1 DNA or its functional equivalent to have the desired effect is assessed by determining whether the transformed phenotype is maintained or reversed after PTPH1 DNA or its functional equivalent is introduced into the transformed cells. Reversal of the phenotype is indicative of the ability of the introduced DNA to counter the effects of the kinase. These effects can also be examined at the level of changes in the phosphorylation state of tyrosyl residues in intracellular proteins.

Transformed cells are transfected with the PTPH1 DNA using an appropriate expression vector. The ability of PTPH1 DNA or its functional equivalent to have the desired effect is assessed by determining whether the transformed phenotype is maintained or reversed. Reversal of the phenotype is indicative of the ability of the introduced DNA to counter the effects of the kinase.

Thus, an agent and a method for preventing or reversing the malignant transformation of cells associated with or caused by the activity of a protein tyrosine kinase are now available. The agent can be DNA or RNA encoding PTPH1 or its functional equivalent. A functional equivalent of PTPH1 has substantially the same sequence as that shown in FIG. 1, and can catalyze dephosphorylation of tyrosyl residues phosphorylated through the action of a protein tyrosine kinase. As used herein, the term PTPH1 includes the protein whose amino acid sequence is represented in FIG. 1 and its functional equivalents, as defined above. Modified or mutated PTPH1-encoding DNA (i.e., DNA which differs from the PTPH1 DNA of FIG. 1 by at least one addition, deletion or substitution) can also be used.

In the method of the present invention, DNA encoding PTPH1 or its functional equivalent is introduced into an individual in whom its effects are desired. It is introduced in a recombinant vehicle, such as, but not limited to, retrovirus or vaccinia virus. All or a portion of the PTPH1 DNA or RNA can be used, provided that it is sufficient. to express in host cells a protein or peptide with the PTPase activity. PTPH1-encoding DNA can be introduced into a retroviral vector, such as those described in the literature, using known-methods (See, for example, Yu et al., *Proc. Natl. Acad. Sci USA,* 83:3194–3198 (1986); Markowitz et al., *J. Virol.,* 62:1120–1124 (1988); Cepko et al., *Cell,* 37:1053–1062 (1984); Mann et al., *Cell,* 33:153–159 (1983); Cone et al., *Proc. Natl. Acad. Sci. USA,* 81:6349–6353 (1984)). Alternatively, it can be introduced into vaccinia virus, using known methods.

The resulting recombinant gene transfer vehicle, which contains all or a portion of the PTPH1 DNA (or RNA), is introduced into an individual in sufficient quantities to prevent malignant transformation associated with phosphorylation of tyrosyl residues in proteins via a protein tyrosine kinase-catalyzed reaction. The PTPH1 DNA-containing vehicle can be introduced by a variety of routes (e.g., intraperitoneally, intramuscularly, intravascularly) and will generally be introduced in combination with a carrier (e.g., physiological saline or suitable buffer). This method is useful in the treatment or prevention of a variety of malignancies, including breast cancer and leukemia.

Exemplification
Identification of PTPH1

Oligonucleotide primers were synthesized based on the conserved sequences KCAQYWP (SEQ ID NO:12) (#1,
equivalent to residues 120–126 in PTP1B) and HCSAGIG (SEQ ID NO:13) (#2, equivalent to residues 214–220 in PTP1B). The degeneracy of the first primer was 64 fold and that of the second 96 fold. Phage DNA of a HeLa cell cDNA library (Stratagene) isolated by the plate lysate method (Sambrook, J. et al., *Molecular Cloning: A Lab Manual,* 2d (1989)) was used as template. Primers were phosphorylated with T4 polynucleotide kinase (New England Biolabs) prior to PCR and were added at a final concentration of 1 $\mu$M to a mixture containing 10 mM Tris-HCl (pH8.4), 50 mM KCl, 1.5 mM MgCl$_2$, 0.01% gelatin, 20 mM dNTPS, 2.5 units Taq polymerase (Perkin-Elmer/Cetus) and 2 $\mu$g phage DNA. Thirty cycles of the PCR reaction were performed; each was carried out at 94° C. for 1 min, 50° C. for 1 min and 72° C. for 2 min. The PCR products were analyzed on a 1% agarose gel and DNA fragments of approximately 0.25 kb were excise, eluted from the gel, subcloned into the SmaI site of pUC118 and sequenced. The same HeLa cDNA library was probed with the 0.25 kb PTPH1 product of PCR obtained above. Plaques were transferred to nitrocellulose filters (Schleicher & Schuell) and screened by hybridization at 65° C. in a solution containing 2×SSC (SSC=0.15M NaCl, 0.015 M trisodium citrate), 5×Denhardt's, 0.1% SDS, 25 mM sodium phosphate, 1% sodium pyrophospate, 10% dextran sulfate and 12.5 $\mu$g/ml denatured calf thymus DNA. The filters were washed successively at the same temperature in a series of solutions containing 0.1% SDS with 4×SSC, 2×SSC, 1×SSC and finally 0.1×SSC. Hybridizing phage were plaque purified, DNA was prepared and cDNA inserts were isolated and subcloned using standard techniques (Sambrook, J. et al., *Molecular Cloning: A Lab Manual,* 2d (1989)). DNA sequencing was carried out by the dideoxynucleotide chain-termination procedure (Sanger, F. et al., *Proc. Natl. Acad. Sci. USA,* 74:5463–5467 (1977)) using either manufacturer's primers (United States Biochemical Corporation) or synthetic oligonucleotides derived from the existing sequences. The GenBank database of sequence information was searched with the FASTA program of Pearson and Lipman to identify proteins with amino acid sequence similar to that of PTPH1.

The nucleotide sequence of the cDNA designated PTPH1 and the predicted amino acid sequence are represented in FIG. 1. The open box delineates the segment of homology to the N-terminal domain of band 4.1, ezrin and talin. The shaded box defines the segment homologous to the catalytic domains of the PTPases. In the intervening segment, seryl and threonyl residues located in sequences bearing features of sites of casein kinase II phosphorylation sites are underlined. The primary structure requirements for casein kinase II phosphorylation include the presence of surrounding acidic residues. An Asp or Glu three residues to the C-terminus of the phosphate acceptor site is particularly critical (Kuenzel, E. A. et al., *J. Biol. Chem.,* 262:9136–9140 (1987)). The presence of prolyl residues preceeding the phosphorylation site is also common. In addition, seryl residues 372 and 381 display some features of potential sites of phosphorylation by p34$^{cdc2}$ (Moreno, S. and P. Nurse, *Cell* 61:549–551 (1990)).

Northern analysis of PTPH1 mRNA was also carried out. Total RNA was extracted from HeLa cells and Poly(A)+ RNA was selected by oligo (dT)-cellulose chromatography as described by Sambrook, J. et al. (Sambrook, J. et al., *Molecular Cloning: A Lab Manual,* 2d (1989)). After electrophoresis on a formaldehyde-agarose (1%) gel, the RNA was transferred to a Gene Screen Plus membrane and hybridized with the 4 kb insert of PTPH1. The hybridization and washing conditions were the same as described above, except that SDS was included at 1%. Results are shown in FIG. 2. Numbers on the right indicate the size of RNA markers (BRL).

The relationship of the structure of PTPH1 was assessed and compared with that of other proteins. This assessment showed that PTPH1 comprises three segments, as represented in FIG. 3: an N-terminal segment (shaded) with homology to the membrane localization domains in band 4.1, ezrin and talin, a putative regulatory segment in the middle of the protein (open) and a C-terminal PTPase related segment (black). TM denotes the transmembrane domain in CD45. The length of each protein is shown in proportion to its molecular weight. The homology among domains is indicated by their percentage identity expressed as the number of identities out of possible matches between residues in the aligned sequences. In addition the numbers in parentheses are alignment scores, which express the similarity of segments in units of standard deviation from the average background scores of 100 randomly generated sequences. The alignments were optimised using the ALIGN programme from the National Biomedical Research Foundation, the mutation data matrix and a gap penalty of 10. Scores of >5 suggest homology. Residues 3–357 in PTPH1 were compared pairwise with 2–323 in band 4.1, 4–339 in ezrin and 120–455 in talin. Residues 669–913 in PTPH1 were compared pairwise with 40–289 in PTP1B, 42–273 in TCPTPase, 491–738 in CD45 domain I and 782–1054 in CD45 domain II.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An antibody specific for a PTPH1 protein, said PTPH1 protein comprising the amino acid sequence set forth in SEQ ID NO:2.

2. The antibody of claim 1, wherein the PTPH1 protein localizes to an interface between a plasma membrane and a cytoskeleton.

3. The antibody of claim 1, wherein the PTPH 1 protein localizes to a focal adhesion.

* * * * *

SEQUENCE LISTING

```
<160> NUMBER OF SEQ ID NOS: 13

<210> SEQ ID NO 1
<211> LENGTH: 3984
<212> TYPE: DNA
<213> ORGANISM: Homosapiens
<220> FEATURE:
<221> NAME/KEY: CDS
<222> LOCATION: (24)...(2765)

<400> SEQUENCE: 1
ctgcaggtta ttcagcgata gtt atg acc tcc cgg tta cgt gcg ttg ggt gga      53
                         Met Thr Ser Arg Leu Arg Ala Leu Gly Gly
                          1               5                  10 aga att aat aat ata cgc acc tcg gag tta ccc aaa gag aaa act cga      101
Arg Ile Asn Asn Ile Arg Thr Ser Glu Leu Pro Lys Glu Lys Thr Arg
             15                  20                  25 tca gaa gtc att tgc agc atc cac ttt tta gat ggc gtg gta cag acc      149
Ser Glu Val Ile Cys Ser Ile His Phe Leu Asp Gly Val Val Gln Thr
         30                  35                  40 ttt aaa gtt act aaa caa gac act ggc cag gtt ctt ctg gat atg gtg      197
Phe Lys Val Thr Lys Gln Asp Thr Gly Gln Val Leu Leu Asp Met Val
     45                  50                  55 cac aac cac ctg ggt gtg act gaa aag gaa tat ttt ggt tta cag cat      245
His Asn His Leu Gly Val Thr Glu Lys Glu Tyr Phe Gly Leu Gln His
 60                  65                  70 gat gac gac tcc gtg gac tct cct aga tgg ctg gaa gca agc aaa ccc      293
Asp Asp Asp Ser Val Asp Ser Pro Arg Trp Leu Glu Ala Ser Lys Pro
 75                  80                  85                  90 atc agg aag cag tta aaa gga ggt ttc ccc tgt acc ctg cat ttt cga      341
Ile Arg Lys Gln Leu Lys Gly Gly Phe Pro Cys Thr Leu His Phe Arg
                 95                 100                 105 gta aga ttt ttt ata cct gat ccc aac aca ctg cag caa gaa caa acc      389
Val Arg Phe Phe Ile Pro Asp Pro Asn Thr Leu Gln Gln Glu Gln Thr
            110                 115                 120 agg cac ttg tat ttc tta caa ctg aag atg gat att tgc gaa gga agg      437
Arg His Leu Tyr Phe Leu Gln Leu Lys Met Asp Ile Cys Glu Gly Arg
        125                 130                 135 tta acc tgc cct ctt aac tca gca gtg gtt cta gcg tcc tat gcc gta      485
Leu Thr Cys Pro Leu Asn Ser Ala Val Val Leu Ala Ser Tyr Ala Val
    140                 145                 150
```

-continued

```
caa tct cat ttt gga gac tat aat tct tcc ata cat cat cca ggc tat      533
Gln Ser His Phe Gly Asp Tyr Asn Ser Ser Ile His His Pro Gly Tyr
155                 160                 165                 170 ctt tcc gat agt cac ttt ata ccc gat caa aat gag gac ttt tta aca      581
Leu Ser Asp Ser His Phe Ile Pro Asp Gln Asn Glu Asp Phe Leu Thr
            175                 180                 185 aaa gtc gaa tct ctg cat gag cag cac agt ggg cta aaa caa tca gaa      629
Lys Val Glu Ser Leu His Glu Gln His Ser Gly Leu Lys Gln Ser Glu
        190                 195                 200 gca gaa tcc tgc tat atc aac ata gcg cgg acc ctc gac ttc tat gga      677
Ala Glu Ser Cys Tyr Ile Asn Ile Ala Arg Thr Leu Asp Phe Tyr Gly
    205                 210                 215 gta gaa ctg cac agt ggt agg gat ctg cac aat tta gac cta atg att      725
Val Glu Leu His Ser Gly Arg Asp Leu His Asn Leu Asp Leu Met Ile
220                 225                 230 gga att gct tcc gcg ggt gtt gct gtg tac cga aaa tac att tgc aca      773
Gly Ile Ala Ser Ala Gly Val Ala Val Tyr Arg Lys Tyr Ile Cys Thr
235                 240                 245                 250 agt ttc tat cct tgg gtg aac att ctc aaa att tct ttc aaa agg aaa      821
Ser Phe Tyr Pro Trp Val Asn Ile Leu Lys Ile Ser Phe Lys Arg Lys
            255                 260                 265 aag ttc ttc ata cat cag cga cag aaa cag gct gaa tcc agg gaa cat      869
Lys Phe Phe Ile His Gln Arg Gln Lys Gln Ala Glu Ser Arg Glu His
        270                 275                 280 att gtg gcc ttc aac atg ctg aat tac cga tct tgc aaa aac ttg tgg      917
Ile Val Ala Phe Asn Met Leu Asn Tyr Arg Ser Cys Lys Asn Leu Trp
    285                 290                 295 aaa tcc tgt gtt gag cac cat acg ttc ttt cag gca aag aag cta cta      965
Lys Ser Cys Val Glu His His Thr Phe Phe Gln Ala Lys Lys Leu Leu
300                 305                 310 cct cag gaa aag aat gtt ctg tct cag tac tgg act atg ggc tct cgg     1013
Pro Gln Glu Lys Asn Val Leu Ser Gln Tyr Trp Thr Met Gly Ser Arg
315                 320                 325                 330 aac acc aaa aag tcg gta aat aac caa tat tgc aaa aag gtg att ggc     1061
Asn Thr Lys Lys Ser Val Asn Asn Gln Tyr Cys Lys Lys Val Ile Gly
            335                 340                 345 ggg atg gtg tgg aac cca gcc atg cgg aga tcc tta tca gtg gag cac     1109
Gly Met Val Trp Asn Pro Ala Met Arg Arg Ser Leu Ser Val Glu His
        350                 355                 360 tta gaa acc aag agt ctg cct tct cgt tcc cct ccc att act ccc aac     1157
Leu Glu Thr Lys Ser Leu Pro Ser Arg Ser Pro Pro Ile Thr Pro Asn
    365                 370                 375 tgg cga agt cct cgg ctc cgg cac gaa atc cga aag cca cgc cac tct     1205
Trp Arg Ser Pro Arg Leu Arg His Glu Ile Arg Lys Pro Arg His Ser
380                 385                 390 tct gca gat aac ctt gca aat gaa atg acc tac atc acg gaa acg gaa     1253
Ser Ala Asp Asn Leu Ala Asn Glu Met Thr Tyr Ile Thr Glu Thr Glu
395                 400                 405                 410 gat gta ttt tac acg tac aag ggc tct ctg gcc cct caa gac agc gat     1301
Asp Val Phe Tyr Thr Tyr Lys Gly Ser Leu Ala Pro Gln Asp Ser Asp
            415                 420                 425 tct gaa gtt tct cag aac cga agc ccg cac caa gag agt tta tcc gag     1349
Ser Glu Val Ser Gln Asn Arg Ser Pro His Gln Glu Ser Leu Ser Glu
        430                 435                 440 aac aat ccg gca caa agc tac ctg acc cag aag tca tcc agt tct gtg     1397
Asn Asn Pro Ala Gln Ser Tyr Leu Thr Gln Lys Ser Ser Ser Ser Val
    445                 450                 455 tct cca tct tca aat gct cca ggc tcc tgc tca cct gac ggc gtt gat     1445
Ser Pro Ser Ser Asn Ala Pro Gly Ser Cys Ser Pro Asp Gly Val Asp
460                 465                 470
```

-continued

| | | |
|---|---|---|
| cag cag ctc tta gat gac ttc cac agg gtg acc aaa ggg ggc tcc acc<br>Gln Gln Leu Leu Asp Asp Phe His Arg Val Thr Lys Gly Gly Ser Thr<br>475                            480                    485                  490 | 1493 |
| gag gac gcc agc cag tac tac tgt gac aag aat gat aat ggt gac agc<br>Glu Asp Ala Ser Gln Tyr Tyr Cys Asp Lys Asn Asp Asn Gly Asp Ser<br>                    495                    500                    505 | 1541 |
| tac tta gtc ttg atc cgt atc aca cca gat gaa gat gga aaa ttt gga<br>Tyr Leu Val Leu Ile Arg Ile Thr Pro Asp Glu Asp Gly Lys Phe Gly<br>              510                    515                    520 | 1589 |
| ttt aat ctt aag gga gga gtg gat caa aag atg cct ctt gtg gta tca<br>Phe Asn Leu Lys Gly Gly Val Asp Gln Lys Met Pro Leu Val Val Ser<br>          525                    530                    535 | 1637 |
| agg ata aac cca gag tca cct gcg gac acc tgc att cct aag ctg aac<br>Arg Ile Asn Pro Glu Ser Pro Ala Asp Thr Cys Ile Pro Lys Leu Asn<br>540                            545                    550 | 1685 |
| gaa ggg gat caa atc gtg tta atc aat ggc cgg gac atc tca gaa cac<br>Glu Gly Asp Gln Ile Val Leu Ile Asn Gly Arg Asp Ile Ser Glu His<br>555                          560                    565                  570 | 1733 |
| acg cat gac caa gtg gtg atg ttc atc aaa gcc agc cgg gag tcc cac<br>Thr His Asp Gln Val Val Met Phe Ile Lys Ala Ser Arg Glu Ser His<br>                    575                    580                    585 | 1781 |
| tca cgg gag ctg gcc ctg gtg atc agg agg aga gct gtc cgc tca ttt<br>Ser Arg Glu Leu Ala Leu Val Ile Arg Arg Arg Ala Val Arg Ser Phe<br>              590                    595                    600 | 1829 |
| gct gac ttc aag tct gaa gat gaa ctg aac cag ctt ttc ccc gaa gcc<br>Ala Asp Phe Lys Ser Glu Asp Glu Leu Asn Gln Leu Phe Pro Glu Ala<br>                    605                    610                    615 | 1877 |
| att ttc ccc atg tgt ccg gag ggt ggg gac act ttg gag gga tcc atg<br>Ile Phe Pro Met Cys Pro Glu Gly Gly Asp Thr Leu Glu Gly Ser Met<br>620                            625                    630 | 1925 |
| gca cag cta aag aag ggc ctc gaa agc ggg acg gtg ctg atc cag ttt<br>Ala Gln Leu Lys Lys Gly Leu Glu Ser Gly Thr Val Leu Ile Gln Phe<br>635                            640                    645                  650 | 1973 |
| gag caa ctc tac aga aaa aag cca ggt ttg gcc atc acg ttt gca aag<br>Glu Gln Leu Tyr Arg Lys Lys Pro Gly Leu Ala Ile Thr Phe Ala Lys<br>                    655                    660                    665 | 2021 |
| ctg cct caa aat ttg gac aaa aac cga tat aaa gat gtg ctg cct tat<br>Leu Pro Gln Asn Leu Asp Lys Asn Arg Tyr Lys Asp Val Leu Pro Tyr<br>                        670                    675                    680 | 2069 |
| gac acc acc cgg gta tta ttg cag gga aat gaa gat tat att aat gca<br>Asp Thr Thr Arg Val Leu Leu Gln Gly Asn Glu Asp Tyr Ile Asn Ala<br>                    685                    690                    695 | 2117 |
| agt tac gtg aac atg gaa att cct gct gct aac ctt gtg aac aag tac<br>Ser Tyr Val Asn Met Glu Ile Pro Ala Ala Asn Leu Val Asn Lys Tyr<br>700                            705                    710 | 2165 |
| atc gcc act cag ggg ccc ctg ccg cat acc tgt gca cag ttt tgg cag<br>Ile Ala Thr Gln Gly Pro Leu Pro His Thr Cys Ala Gln Phe Trp Gln<br>715                            720                    725                  730 | 2213 |
| gtt gtc tgg gat cag aag ttg tca ctc att gtc atg ttg acg act ctc<br>Val Val Trp Asp Gln Lys Leu Ser Leu Ile Val Met Leu Thr Thr Leu<br>                    735                    740                    745 | 2261 |
| aca gaa cga ggg cgg acc aaa tgt cac cag tac tgg cca gat ccc ccc<br>Thr Glu Arg Gly Arg Thr Lys Cys His Gln Tyr Trp Pro Asp Pro Pro<br>                    750                    755                    760 | 2309 |
| gac gtc atg aac cac ggc ggc ttt cac atc cag tgt cag tca gag gac<br>Asp Val Met Asn His Gly Gly Phe His Ile Gln Cys Gln Ser Glu Asp<br>                    765                    770                    775 | 2357 |
| tgc acc atc gcc tat gtg tcc cga gaa atg ctg gtc aca aac acc cag<br>Cys Thr Ile Ala Tyr Val Ser Arg Glu Met Leu Val Thr Asn Thr Gln<br>780                            785                    790 | 2405 |

-continued

```
acc ggg gaa gaa cac aca gtg aca cat ctc cag tac gtc gca tgg cct      2453
Thr Gly Glu Glu His Thr Val Thr His Leu Gln Tyr Val Ala Trp Pro
795                 800                 805                 810 gac cac ggt ata ccc gat gac tcc tcc gac ttt ctg gaa ttt gta aac      2501
Asp His Gly Ile Pro Asp Asp Ser Ser Asp Phe Leu Glu Phe Val Asn
            815                 820                 825 tat gtg agg tct ctg aga gtg gac agc gag cct gtc cta gtt cac tgc      2549
Tyr Val Arg Ser Leu Arg Val Asp Ser Glu Pro Val Leu Val His Cys
        830                 835                 840 agt gct gga ata ggt cga acc ggt gtg ttg gtc act atg gaa aca gcc      2597
Ser Ala Gly Ile Gly Arg Thr Gly Val Leu Val Thr Met Glu Thr Ala
    845                 850                 855 atg tgc cta act gag agg aac ctg ccc att tac cca ctg gat att gtc      2645
Met Cys Leu Thr Glu Arg Asn Leu Pro Ile Tyr Pro Leu Asp Ile Val
860                 865                 870 cga aaa atg cga gac cag cgc gcc atg atg gtg cag aca tca agc cag      2693
Arg Lys Met Arg Asp Gln Arg Ala Met Met Val Gln Thr Ser Ser Gln
875                 880                 885                 890 tac aag ttt gtg tgt gaa gcg att ctt cgt gtg tat gaa gaa ggt tta      2741
Tyr Lys Phe Val Cys Glu Ala Ile Leu Arg Val Tyr Glu Glu Gly Leu
            895                 900                 905 gtc caa atg ctg gat cct agt taa gacaactgtg aaaaagttca ttcctctttc     2795
Val Gln Met Leu Asp Pro Ser *
            910 ccaagggcat cctccttgaa agaggaggac agacctctct ggaagcagca agaggaacca    2855 gtagctgtgg gaaaggaatg ggcacctctg aacccaggca ctttaaactt ctatagaaaa    2915 gatatcgtgt acataggaac tggtgtagat aagcatgcaa ttatggcatc atttaggcct    2975 gtatttctat ggaaagatac aaaaaggatc tcagtttggg gcctgtccta atgccttctt    3035 ccctaacatc accacacaca cccctgtcgg catcctggag caattgagac cggacaccca    3095 cagagctgtt gtcctcccag caacaagatg gtgtggttat cttgggtcat ttggatgttt    3155 tgtttgtttc tgtgtgtcag actgtaaggg ctgagctttc tgtgcttcta ggtggagctg    3215 gaacaattca gattcacccg ccctgatgct aaggaaaccc tgacgtatgt actagatggc    3275 agggcactgg gggtcaggct gaaggctgag caacacctct ctgccctccc tccctttgtc    3335 ccatctccca gcgacttcca atattcatgt ttctgagaat tgtgtccctc ttcagttccc    3395 tcttggtgcc taacctggat tagtaatgtg cattcaggtg aattttcagc tgaggctctg    3455 agaactggta ctctcagtgt gttctggtca tcttgtggct tagttgtaga agcaggtgtg    3515 tctcttgcct ctgcttgcct cctactgcac actcagcacc caggactgga atcaccgact    3575 actgaatctc ctacatgtat tgctgctact tcaagctcct ccacttgaaa ccttatgatt    3635 ttccaagggg agatgggaca gtgtcatcta aatattccga atgtttggcc ttctgagaaa    3695 agagcttcta gtaattgaac catgggtttc ccagcttctg gagggttggc cgtgggctgt    3755 gtacatgtgt gtgcccaggg gtgagtgttt ctcaggattc ctaacgattc aaattaccgt    3815 tgagtatata taaagaatcg agtcggaaga acaaatgtgt gcattcaccc ccagtcacaa    3875 tggtctccat tgcatttcaa aggagaggat cagactatct gaatataaac acaatctgat    3935 gttaatttat tctaagaaca ccatctgtat tcattttgat tgtcctaaa              3984
```

<210> SEQ ID NO 2
<211> LENGTH: 913
<212> TYPE: PRT
<213> ORGANISM: Homosapiens

-continued

```
<400> SEQUENCE: 2

Met Thr Ser Arg Leu Arg Ala Leu Gly Gly Arg Ile Asn Asn Ile Arg
 1               5                  10                  15

Thr Ser Glu Leu Pro Lys Glu Lys Thr Arg Ser Glu Val Ile Cys Ser
            20                  25                  30

Ile His Phe Leu Asp Gly Val Val Gln Thr Phe Lys Val Thr Lys Gln
        35                  40                  45

Asp Thr Gly Gln Val Leu Leu Asp Met Val His Asn His Leu Gly Val
 50                  55                  60

Thr Glu Lys Glu Tyr Phe Gly Leu Gln His Asp Asp Ser Val Asp
 65                  70                  75                  80

Ser Pro Arg Trp Leu Glu Ala Ser Lys Pro Ile Arg Lys Gln Leu Lys
                85                  90                  95

Gly Gly Phe Pro Cys Thr Leu His Phe Arg Val Arg Phe Phe Ile Pro
            100                 105                 110

Asp Pro Asn Thr Leu Gln Gln Glu Gln Thr Arg His Leu Tyr Phe Leu
        115                 120                 125

Gln Leu Lys Met Asp Ile Cys Glu Gly Arg Leu Thr Cys Pro Leu Asn
130                 135                 140

Ser Ala Val Val Leu Ala Ser Tyr Ala Val Gln Ser His Phe Gly Asp
145                 150                 155                 160

Tyr Asn Ser Ser Ile His His Pro Gly Tyr Leu Ser Asp Ser His Phe
                165                 170                 175

Ile Pro Asp Gln Asn Glu Asp Phe Leu Thr Lys Val Glu Ser Leu His
            180                 185                 190

Glu Gln His Ser Gly Leu Lys Gln Ser Glu Ala Glu Ser Cys Tyr Ile
        195                 200                 205

Asn Ile Ala Arg Thr Leu Asp Phe Tyr Gly Val Glu Leu His Ser Gly
210                 215                 220

Arg Asp Leu His Asn Leu Asp Leu Met Ile Gly Ile Ala Ser Ala Gly
225                 230                 235                 240

Val Ala Val Tyr Arg Lys Tyr Ile Cys Thr Ser Phe Tyr Pro Trp Val
                245                 250                 255

Asn Ile Leu Lys Ile Ser Phe Lys Arg Lys Lys Phe Phe Ile His Gln
            260                 265                 270

Arg Gln Lys Gln Ala Glu Ser Arg Glu His Ile Val Ala Phe Asn Met
        275                 280                 285

Leu Asn Tyr Arg Ser Cys Lys Asn Leu Trp Lys Ser Cys Val Glu His
290                 295                 300

His Thr Phe Phe Gln Ala Lys Lys Leu Leu Pro Gln Glu Lys Asn Val
305                 310                 315                 320

Leu Ser Gln Tyr Trp Thr Met Gly Ser Arg Asn Thr Lys Lys Ser Val
                325                 330                 335

Asn Asn Gln Tyr Cys Lys Lys Val Ile Gly Gly Met Val Trp Asn Pro
            340                 345                 350

Ala Met Arg Arg Ser Leu Ser Val Glu His Leu Glu Thr Lys Ser Leu
        355                 360                 365

Pro Ser Arg Ser Pro Pro Ile Thr Pro Asn Trp Arg Ser Pro Arg Leu
370                 375                 380

Arg His Glu Ile Arg Lys Pro Arg His Ser Ser Ala Asp Asn Leu Ala
385                 390                 395                 400

Asn Glu Met Thr Tyr Ile Thr Glu Thr Glu Asp Val Phe Tyr Thr Tyr
                405                 410                 415
```

-continued

```
Lys Gly Ser Leu Ala Pro Gln Asp Ser Asp Ser Glu Val Ser Gln Asn
            420                 425                 430

Arg Ser Pro His Gln Glu Ser Leu Ser Glu Asn Asn Pro Ala Gln Ser
            435                 440                 445

Tyr Leu Thr Gln Lys Ser Ser Ser Val Ser Pro Ser Ser Asn Ala
            450                 455                 460

Pro Gly Ser Cys Ser Pro Asp Gly Val Asp Gln Gln Leu Leu Asp Asp
465                 470                 475                 480

Phe His Arg Val Thr Lys Gly Gly Ser Thr Glu Asp Ala Ser Gln Tyr
                    485                 490                 495

Tyr Cys Asp Lys Asn Asp Asn Gly Asp Ser Tyr Leu Val Leu Ile Arg
            500                 505                 510

Ile Thr Pro Asp Glu Asp Gly Lys Phe Gly Phe Asn Leu Lys Gly Gly
            515                 520                 525

Val Asp Gln Lys Met Pro Leu Val Val Ser Arg Ile Asn Pro Glu Ser
            530                 535                 540

Pro Ala Asp Thr Cys Ile Pro Lys Leu Asn Glu Gly Asp Gln Ile Val
545                 550                 555                 560

Leu Ile Asn Gly Arg Asp Ile Ser Glu His Thr His Asp Gln Val Val
                    565                 570                 575

Met Phe Ile Lys Ala Ser Arg Glu Ser His Ser Arg Glu Leu Ala Leu
            580                 585                 590

Val Ile Arg Arg Arg Ala Val Arg Ser Phe Ala Asp Phe Lys Ser Glu
            595                 600                 605

Asp Glu Leu Asn Gln Leu Phe Pro Glu Ala Ile Phe Pro Met Cys Pro
            610                 615                 620

Glu Gly Gly Asp Thr Leu Glu Gly Ser Met Ala Gln Leu Lys Lys Gly
625                 630                 635                 640

Leu Glu Ser Gly Thr Val Leu Ile Gln Phe Glu Gln Leu Tyr Arg Lys
                    645                 650                 655

Lys Pro Gly Leu Ala Ile Thr Phe Ala Lys Leu Pro Gln Asn Leu Asp
            660                 665                 670

Lys Asn Arg Tyr Lys Asp Val Leu Pro Tyr Asp Thr Thr Arg Val Leu
            675                 680                 685

Leu Gln Gly Asn Glu Asp Tyr Ile Asn Ala Ser Tyr Val Asn Met Glu
            690                 695                 700

Ile Pro Ala Ala Asn Leu Val Asn Lys Tyr Ile Ala Thr Gln Gly Pro
705                 710                 715                 720

Leu Pro His Thr Cys Ala Gln Phe Trp Gln Val Val Trp Asp Gln Lys
                    725                 730                 735

Leu Ser Leu Ile Val Met Leu Thr Thr Leu Thr Glu Arg Gly Arg Thr
            740                 745                 750

Lys Cys His Gln Tyr Trp Pro Asp Pro Asp Val Met Asn His Gly
            755                 760                 765

Gly Phe His Ile Gln Cys Gln Ser Glu Asp Cys Thr Ile Ala Tyr Val
            770                 775                 780

Ser Arg Glu Met Leu Val Thr Asn Thr Gln Thr Gly Glu Glu His Thr
785                 790                 795                 800

Val Thr His Leu Gln Tyr Val Ala Trp Pro Asp His Gly Ile Pro Asp
                    805                 810                 815

Asp Ser Ser Asp Phe Leu Glu Phe Val Asn Tyr Val Arg Ser Leu Arg
            820                 825                 830
```

```
Val Asp Ser Glu Pro Val Leu Val His Cys Ser Ala Gly Ile Gly Arg
            835                 840                 845

Thr Gly Val Leu Val Thr Met Glu Thr Ala Met Cys Leu Thr Glu Arg
            850                 855                 860

Asn Leu Pro Ile Tyr Pro Leu Asp Ile Val Arg Lys Met Arg Asp Gln
865                 870                 875                 880

Arg Ala Met Met Val Gln Thr Ser Ser Gln Tyr Lys Phe Val Cys Glu
                    885                 890                 895

Ala Ile Leu Arg Val Tyr Glu Glu Gly Leu Val Gln Met Leu Asp Pro
                900                 905                 910

Ser

<210> SEQ ID NO 3
<211> LENGTH: 328
<212> TYPE: PRT
<213> ORGANISM: Homosapiens

<400> SEQUENCE: 3

Ile Cys Ser Ile His Phe Leu Asp Gly Val Gln Thr Phe Lys Val
  1               5                  10                  15

Thr Lys Gln Asp Thr Gly Gln Val Leu Leu Asp Met Val His Asn His
                 20                  25                  30

Leu Gly Val Thr Glu Lys Glu Tyr Phe Gly Leu Gln His Asp Asp Asp
                 35                  40                  45

Ser Val Asp Ser Pro Arg Trp Leu Glu Ala Ser Lys Pro Ile Arg Lys
 50                  55                  60

Gln Leu Lys Gly Gly Phe Pro Cys Thr Leu His Phe Arg Val Arg Phe
65                   70                  75                  80

Phe Ile Pro Asp Pro Asn Thr Leu Gln Gln Glu Gln Thr Arg His Leu
                 85                  90                  95

Tyr Phe Leu Gln Leu Lys Met Asp Ile Cys Glu Gly Arg Leu Thr Cys
                100                 105                 110

Pro Leu Asn Ser Ala Val Val Leu Ala Ser Tyr Ala Val Gln Ser His
                115                 120                 125

Phe Gly Asp Tyr Asn Ser Ser Ile His His Pro Gly Tyr Leu Ser Asp
                130                 135                 140

Ser His Phe Ile Pro Asp Gln Asn Glu Asp Phe Leu Thr Lys Val Glu
145                 150                 155                 160

Ser Leu His Glu Gln His Ser Gly Leu Lys Gln Ser Glu Ala Glu Ser
                165                 170                 175

Cys Tyr Ile Asn Ile Ala Arg Thr Leu Asp Phe Tyr Gly Val Glu Leu
                180                 185                 190

His Ser Gly Arg Asp Leu His Asn Leu Asp Leu Met Ile Gly Ile Ala
                195                 200                 205

Ser Ala Gly Val Ala Val Tyr Arg Lys Tyr Ile Cys Thr Ser Phe Tyr
                210                 215                 220

Pro Trp Val Asn Ile Leu Lys Ile Ser Phe Lys Arg Lys Lys Phe Phe
225                 230                 235                 240

Ile His Gln Arg Gln Lys Gln Ala Glu Ser Arg Glu His Ile Val Ala
                245                 250                 255

Phe Asn Met Leu Asn Tyr Arg Ser Cys Lys Asn Leu Trp Lys Ser Cys
                260                 265                 270

Val Glu His His Thr Phe Gln Ala Lys Lys Leu Leu Pro Gln Glu
                275                 280                 285
```

```
Lys Asn Val Leu Ser Gln Tyr Trp Thr Met Gly Ser Arg Asn Thr Lys
    290                 295                 300

Lys Ser Val Asn Asn Gln Tyr Cys Lys Val Ile Gly Gly Met Val
305                 310                 315                 320

Trp Asn Pro Ala Met Arg Arg Ser
                325
```

<210> SEQ ID NO 4
<211> LENGTH: 322
<212> TYPE: PRT
<213> ORGANISM: Homosapiens

<400> SEQUENCE: 4

```
His Cys Lys Val Ser Leu Leu Asp Asp Thr Val Tyr Glu Cys Val Val
  1               5                  10                  15

Glu Lys His Ala Lys Gly Gln Asp Leu Leu Lys Arg Val Cys Glu His
                20                  25                  30

Leu Asn Leu Leu Glu Glu Asp Tyr Phe Gly Leu Ala Ile Trp Asp Asn
            35                  40                  45

Ala Thr Ser Lys Thr Trp Leu Asp Ser Ala Lys Glu Ile Lys Lys Gln
        50                  55                  60

Val Arg Gly Val Pro Trp Asn Phe Thr Phe Asn Val Lys Phe Tyr Pro
 65                  70                  75                  80

Pro Asp Pro Ala Gln Leu Thr Glu Asp Ile Thr Arg Tyr Tyr Leu Cys
                 85                  90                  95

Leu Gln Leu Arg Gln Asp Ile Val Ala Gly Arg Leu Pro Cys Ser Phe
            100                 105                 110

Ala Thr Leu Ala Leu Leu Gly Ser Tyr Thr Ile Gln Ser Glu Leu Gly
        115                 120                 125

Asp Tyr Asp Pro Glu Leu His Gly Val Asp Tyr Val Ser Asp Phe Lys
130                 135                 140

Leu Ala Pro Asn Gln Thr Lys Glu Leu Glu Glu Lys Val Met Glu Leu
145                 150                 155                 160

His Lys Ser Tyr Arg Ser Met Thr Pro Ala Gln Ala Asp Leu Glu Phe
                165                 170                 175

Leu Glu Asn Ala Lys Lys Leu Ser Met Tyr Gly Val Asp Leu His Lys
            180                 185                 190

Ala Lys Asp Leu Glu Gly Val Asp Ile Ile Leu Gly Val Cys Ser Ser
        195                 200                 205

Gly Leu Leu Val Tyr Lys Asp Lys Leu Arg Ile Asn Arg Phe Pro Trp
210                 215                 220

Pro Lys Val Leu Lys Ile Ser Tyr Lys Arg Ser Ser Phe Phe Ile Lys
225                 230                 235                 240

Ile Arg Pro Gly Glu Gln Glu Gln Tyr Glu Ser Thr Ile Gly Phe Lys
                245                 250                 255

Leu Pro Ser Tyr Arg Ala Ala Lys Lys Leu Trp Lys Val Cys Val Glu
            260                 265                 270

His His Thr Thr Phe Arg Leu Thr Ser Thr Asp Thr Ile Pro Lys Ser
        275                 280                 285

Lys Phe Leu Ala Leu Gly Ser Lys Phe Arg Tyr Ser Gly Arg Thr Gln
        290                 295                 300

Ala Gln Thr Arg Gln Ala Ser Ala Leu Ile Asp Arg Pro Ala Pro His
305                 310                 315                 320

Phe Glu
```

```
<210> SEQ ID NO 5
<211> LENGTH: 336
<212> TYPE: PRT
<213> ORGANISM: Homosapiens

<400> SEQUENCE: 5

Ile Asn Val Arg Val Thr Thr Met Asp Ala Glu Leu Glu Phe Ala Ile
 1               5                  10                  15

Gln Pro Asn Thr Thr Gly Lys Gln Leu Phe Asp Gln Val Val Lys Thr
            20                  25                  30

Ile Gly Leu Arg Glu Val Trp Tyr Phe Gly Leu His Tyr Val Asp Asn
        35                  40                  45

Lys Gly Phe Pro Thr Trp Leu Lys Leu Asp Lys Lys Val Ser Ala Gln
    50                  55                  60

Glu Val Arg Lys Glu Asn Pro Leu Gln Phe Lys Phe Arg Ala Lys Phe
65                  70                  75                  80

Tyr Pro Glu Asp Val Ala Glu Glu Leu Ile Gln Asp Ile Thr Gln Lys
                85                  90                  95

Leu Phe Phe Leu Gln Val Lys Glu Gly Ile Leu Ser Asp Glu Ile Tyr
            100                 105                 110

Cys Pro Pro Glu Thr Ala Val Leu Leu Gly Ser Tyr Ala Val Gln Ala
        115                 120                 125

Lys Phe Gly Asp Tyr Asn Lys Glu Val His Lys Ser Gly Tyr Leu Ser
    130                 135                 140

Ser Glu Arg Leu Ile Pro Gln Arg Val Met Asp Gln His Lys Leu Thr
145                 150                 155                 160

Arg Asp Gln Trp Glu Asp Arg Ile Gln Val Trp His Ala Glu His Arg
                165                 170                 175

Gly Met Leu Lys Asp Asn Ala Met Leu Glu Tyr Leu Lys Ile Ala Gln
            180                 185                 190

Asp Leu Glu Met Tyr Gly Ile Asn Tyr Phe Glu Ile Lys Asn Lys Lys
        195                 200                 205

Gly Thr Asp Leu Trp Leu Gly Val Asp Ala Leu Gly Leu Asn Ile Tyr
    210                 215                 220

Glu Lys Asp Asp Lys Leu Thr Pro Lys Ile Gly Phe Pro Trp Ser Glu
225                 230                 235                 240

Ile Arg Asn Ile Ser Phe Asn Asp Lys Lys Phe Val Ile Lys Pro Ile
                245                 250                 255

Asp Lys Lys Ala Pro Asp Phe Val Phe Tyr Ala Pro Arg Leu Arg Ile
            260                 265                 270

Asn Lys Arg Ile Leu Gln Leu Cys Met Gly Asn His Glu Leu Tyr Met
        275                 280                 285

Arg Arg Arg Lys Pro Asp Thr Ile Glu Val Gln Gln Met Lys Ala Gln
    290                 295                 300

Ala Arg Glu Glu Lys His Gln Lys Gln Leu Glu Arg Gln Leu Glu
305                 310                 315                 320

Thr Glu Lys Lys Arg Arg Glu Thr Val Glu Arg Glu Lys Glu Gln Met
                325                 330                 335

<210> SEQ ID NO 6
<211> LENGTH: 336
<212> TYPE: PRT
<213> ORGANISM: Mus musculus
```

-continued

```
<400> SEQUENCE: 6

Gly Ile Thr Asn His Asp Glu Tyr Ser Leu Val Arg Glu Leu Met Glu
1               5                   10                  15

Glu Lys Lys Asp Glu Gly Thr Gly Thr Leu Arg Lys Asp Lys Thr Leu
            20                  25                  30

Leu Arg Asp Glu Lys Lys Met Glu Lys Leu Lys Gln Lys Leu His Thr
        35                  40                  45

Asp Asp Glu Leu Asn Trp Leu Asp His Gly Arg Thr Leu Arg Glu Gln
50                  55                  60

Gly Val Glu Glu His Glu Thr Leu Leu Leu Arg Arg Lys Phe Phe Tyr
65                  70                  75                  80

Ser Asp Gln Asn Val Asp Ser Arg Asp Pro Val Gln Leu Asn Leu Leu
                85                  90                  95

Tyr Val Gln Ala Arg Asp Asp Ile Leu Asn Gly Ser His Pro Val Ser
            100                 105                 110

Pro Asp Lys Ala Cys Glu Phe Ala Gly Phe Gln Cys Gln Ile Gln Phe
        115                 120                 125

Gly Pro His Asn Glu Gln Lys His Lys Ala Gly Phe Leu Asp Leu Lys
    130                 135                 140

Asp Phe Leu Pro Lys Glu Tyr Val Lys Gln Lys Gly Glu Arg Lys Ile
145                 150                 155                 160

Phe Gln Ala His Lys Asn Cys Gly Gln Met Ser Glu Ile Glu Ala Lys
                165                 170                 175

Val Arg Tyr Val Lys Leu Ala Arg Ser Leu Lys Thr Tyr Gly Val Ser
            180                 185                 190

Phe Phe Leu Val Lys Glu Lys Met Lys Gly Lys Asn Lys Leu Val Pro
        195                 200                 205

Arg Leu Leu Gly Ile Thr Lys Glu Cys Val Met Arg Val Asp Glu Lys
    210                 215                 220

Thr Lys Glu Val Ile Gln Glu Trp Ser Leu Thr Asn Ile Lys Arg Trp
225                 230                 235                 240

Ala Ala Ser Pro Lys Ser Phe Thr Leu Asp Phe Gly Asp Tyr Gln Asp
                245                 250                 255

Gly Tyr Tyr Ser Val Gln Thr Thr Glu Gly Glu Gln Ile Ala Gln Leu
            260                 265                 270

Ile Ala Gly Tyr Ile Asp Ile Ile Leu Lys Lys Lys Ser Lys Asp
        275                 280                 285

His Phe Gly Leu Glu Gly Asp Glu Ser Thr Met Leu Glu Asp Ser
    290                 295                 300

Val Ser Pro Lys Lys Ser Thr Val Leu Gln Gln Gln Tyr Asn Arg Val
305                 310                 315                 320

Gly Lys Val Glu His Gly Ser Val Ala Leu Pro Ala Ile Met Arg Ser
                325                 330                 335

<210> SEQ ID NO 7
<211> LENGTH: 244
<212> TYPE: PRT
<213> ORGANISM: Homosapiens

<400> SEQUENCE: 7

Asn Leu Asp Lys Asn Arg Tyr Lys Asp Val Leu Pro Tyr Asp Thr Thr
1               5                   10                  15

Arg Val Leu Leu Gln Gly Asn Glu Asp Tyr Ile Asn Ala Ser Tyr Val
            20                  25                  30
```

```
Asn Met Glu Ile Pro Ala Ala Asn Leu Val Asn Lys Tyr Ile Ala Thr
            35                  40                  45
Gln Gly Pro Leu Pro His Thr Cys Ala Gln Phe Trp Gln Val Val Trp
 50                  55                  60
Asp Gln Lys Leu Ser Leu Ile Val Met Leu Thr Thr Leu Thr Glu Arg
65                  70                  75                  80
Gly Arg Thr Lys Cys His Gln Tyr Trp Pro Asp Pro Asp Val Met
                85                  90                  95
Asn His Gly Gly Phe His Ile Gln Cys Gln Ser Glu Asp Cys Thr Ile
            100                 105                 110
Ala Tyr Val Ser Arg Glu Met Leu Val Thr Asn Thr Gln Thr Gly Glu
            115                 120                 125
Glu His Thr Val Thr His Leu Gln Tyr Val Ala Trp Pro Asp His Gly
            130                 135                 140
Ile Pro Asp Asp Ser Ser Asp Phe Leu Glu Phe Val Asn Tyr Val Arg
145                 150                 155                 160
Ser Leu Arg Val Asp Ser Glu Pro Val Leu Val His Cys Ser Ala Gly
                165                 170                 175
Ile Gly Arg Thr Gly Val Leu Val Thr Met Glu Thr Ala Met Cys Leu
            180                 185                 190
Thr Glu Arg Asn Leu Pro Ile Tyr Pro Leu Asp Ile Val Arg Lys Met
            195                 200                 205
Arg Asp Gln Arg Ala Met Met Val Gln Thr Ser Ser Gln Tyr Lys Phe
210                 215                 220
Val Cys Glu Ala Ile Leu Arg Val Tyr Glu Glu Gly Leu Val Gln Met
225                 230                 235                 240
Leu Asp Pro Ser

<210> SEQ ID NO 8
<211> LENGTH: 250
<212> TYPE: PRT
<213> ORGANISM: Homosapiens

<400> SEQUENCE: 8

Asn Lys Asn Arg Asn Arg Tyr Arg Asp Val Ser Pro Phe Asp His Ser
 1               5                  10                  15
Arg Ile Lys Leu His Gln Glu Asp Asn Asp Tyr Ile Asn Ala Ser Leu
                20                  25                  30
Ile Lys Met Glu Glu Ala Gln Arg Ser Tyr Ile Leu Thr Gln Gly Pro
            35                  40                  45
Leu Pro Asn Thr Cys Gly His Phe Trp Glu Met Val Trp Glu Gln Lys
 50                  55                  60
Ser Arg Gly Val Val Met Leu Asn Arg Val Met Glu Lys Gly Ser Leu
65                  70                  75                  80
Lys Cys Ala Gln Tyr Trp Pro Gln Lys Glu Glu Lys Glu Met Ile Phe
                85                  90                  95
Glu Asp Thr Asn Leu Lys Leu Thr Leu Ile Ser Glu Asp Ile Lys Ser
            100                 105                 110
Tyr Tyr Thr Val Arg Gln Leu Glu Leu Glu Asn Leu Thr Thr Gln Glu
            115                 120                 125
Thr Arg Glu Ile Leu His Phe His Tyr Thr Thr Trp Pro Asp Phe Gly
            130                 135                 140
Val Pro Glu Ser Pro Ala Ser Phe Leu Asn Phe Leu Phe Lys Val Arg
145                 150                 155                 160
```

```
Glu Ser Gly Ser Leu Ser Pro Glu His Gly Pro Val Val His Cys
            165                 170                 175

Ser Ala Gly Ile Gly Arg Ser Gly Thr Phe Cys Leu Ala Asp Thr Cys
            180                 185                 190

Leu Leu Leu Met Asp Lys Arg Lys Asp Pro Ser Ser Val Asp Ile Lys
            195                 200                 205

Lys Val Leu Leu Glu Met Arg Lys Phe Arg Met Gly Leu Ile Gln Thr
            210                 215                 220

Ala Asp Gln Leu Arg Phe Ser Tyr Leu Ala Val Ile Glu Gly Ala Lys
225                 230                 235                 240

Phe Ile Met Gly Asp Ser Ser Val Gln Asp
                245                 250

<210> SEQ ID NO 9
<211> LENGTH: 246
<212> TYPE: PRT
<213> ORGANISM: Homosapiens

<400> SEQUENCE: 9

Asn Arg Asn Arg Asn Arg Tyr Arg Asp Val Ser Pro Tyr Asp His Ser
1               5                   10                  15

Arg Val Lys Leu Gln Asn Ala Glu Asn Asp Tyr Ile Asn Ala Ser Leu
            20                  25                  30

Val Asp Ile Glu Glu Ala Gln Arg Ser Tyr Ile Leu Thr Gln Gly Pro
            35                  40                  45

Leu Pro Asn Thr Cys Cys His Phe Trp Leu Met Val Trp Gln Gln Lys
        50                  55                  60

Thr Lys Ala Val Val Met Leu Asn Arg Ile Val Glu Lys Glu Ser Val
65              70                  75                  80

Lys Cys Ala Gln Tyr Trp Pro Thr Asp Gln Glu Met Leu Phe Lys
            85                  90                  95

Glu Thr Gly Phe Ser Val Lys Leu Leu Ser Glu Asp Val Lys Ser Tyr
            100                 105                 110

Tyr Thr Val His Leu Leu Gln Leu Glu Asn Ile Asn Ser Gly Glu Thr
            115                 120                 125

Arg Thr Ile Ser His Phe His Tyr Thr Thr Trp Pro Asp Phe Gly Val
            130                 135                 140

Pro Glu Ser Pro Ala Ser Phe Leu Asn Phe Leu Phe Lys Val Arg Glu
145                 150                 155                 160

Ser Gly Ser Leu Asn Pro Asp His Gly Pro Ala Val Ile His Cys Ser
            165                 170                 175

Ala Gly Ile Gly Arg Ser Gly Thr Phe Ser Leu Val Asp Thr Cys Leu
            180                 185                 190

Val Leu Met Glu Lys Gly Asp Asp Ile Asn Ile Lys Gln Val Leu Leu
            195                 200                 205

Asn Met Arg Lys Tyr Arg Met Gly Leu Ile Gln Thr Pro Asp Gln Leu
            210                 215                 220

Arg Phe Ser Tyr Met Ala Ile Ile Glu Gly Ala Lys Cys Ile Lys Gly
225                 230                 235                 240

Asp Ser Ser Ile Gln Lys
                245

<210> SEQ ID NO 10
<211> LENGTH: 248
<212> TYPE: PRT
<213> ORGANISM: Homosapiens
```

-continued

```
<400> SEQUENCE: 10

Asn Gln Asn Lys Asn Arg Tyr Val Asp Ile Leu Pro Tyr Asp Tyr Asn
  1               5                  10                  15

Arg Val Glu Leu Ser Glu Ile Asn Gly Asp Ala Gly Ser Asn Tyr Ile
             20                  25                  30

Asn Ala Ser Tyr Ile Asp Gly Phe Lys Glu Pro Arg Lys Tyr Ile Ala
         35                  40                  45

Ala Gln Gly Pro Arg Asp Glu Thr Val Asp Asp Phe Trp Arg Met Ile
     50                  55                  60

Trp Glu Gln Lys Ala Thr Val Ile Val Met Val Thr Arg Cys Glu Glu
 65                  70                  75                  80

Gly Asn Arg Asn Lys Cys Ala Glu Tyr Trp Pro Ser Met Glu Glu Gly
                 85                  90                  95

Thr Arg Ala Phe Gly Asp Val Val Lys Ile Asn Gln His Lys Arg
             100                 105                 110

Cys Pro Asp Tyr Ile Ile Gln Lys Leu Asn Ile Val Asn Lys Lys Glu
             115                 120                 125

Lys Ala Thr Gly Arg Glu Val Thr His Ile Gln Phe Thr Ser Trp Pro
    130                 135                 140

Asp His Gly Val Pro Glu Asp Pro His Leu Leu Leu Lys Leu Arg Arg
145                 150                 155                 160

Arg Val Asn Ala Phe Ser Asn Phe Phe Ser Gly Pro Ile Val Val His
                165                 170                 175

Cys Ser Ala Gly Val Gly Arg Thr Gly Thr Tyr Ile Gly Ile Asp Ala
            180                 185                 190

Met Leu Glu Gly Leu Glu Ala Glu Asn Lys Val Asp Val Tyr Gly Tyr
            195                 200                 205

Val Val Lys Leu Arg Arg Gln Arg Cys Leu Met Val Gln Val Glu Ala
        210                 215                 220

Gln Tyr Ile Leu Ile His Gln Ala Leu Val Glu Tyr Asn Gln Arg Gly
225                 230                 235                 240

Glu Thr Glu Val Asn Leu Ser Glu
                245

<210> SEQ ID NO 11
<211> LENGTH: 273
<212> TYPE: PRT
<213> ORGANISM: Homosapiens

<400> SEQUENCE: 11

Asn Lys Ser Lys Asn Arg Asn Ser Asn Val Ile Pro Tyr Asp Tyr Asn
  1               5                  10                  15

Arg Val Pro Leu Lys His Glu Leu Glu Met Ser Lys Glu Ser Glu His
             20                  25                  30

Asp Ser Asp Glu Ser Ser Asp Asp Ser Asp Ser Glu Pro Ser
         35                  40                  45

Lys Tyr Ile Asn Ala Ser Phe Ile Met Ser Tyr Trp Lys Pro Glu Val
     50                  55                  60

Met Ile Ala Ala Gln Gly Pro Leu Lys Glu Thr Ile Gly Asp Phe Trp
 65                  70                  75                  80

Gln Met Ile Phe Gln Arg Lys Val Lys Val Ile Val Met Leu Thr Glu
                 85                  90                  95

Leu Lys His Gly Asp Gln Glu Ile Cys Ala Gln Tyr Trp Gly Glu Gly
             100                 105                 110
```

-continued

```
Lys Gln Thr Tyr Gly Asp Ile Glu Val Asp Leu Lys Asp Thr Asp Lys
        115                 120                 125

Ser Ser Thr Tyr Thr Leu Arg Val Phe Glu Leu Arg His Ser Lys Arg
        130                 135                 140

Lys Asp Ser Arg Thr Val Tyr Gln Tyr Gln Tyr Thr Asn Trp Ser Val
145                 150                 155                 160

Glu Gln Leu Pro Ala Glu Pro Lys Glu Leu Ile Ser Met Ile Gln Val
                165                 170                 175

Val Lys Gln Lys Leu Pro Gln Lys Asn Ser Ser Glu Gly Asn Lys His
                180                 185                 190

His Lys Ser Thr Pro Leu Leu Ile His Cys Arg Asp Gly Ser Gln Gln
        195                 200                 205

Thr Gly Ile Phe Cys Ala Leu Leu Asn Leu Leu Glu Ser Ala Glu Thr
        210                 215                 220

Glu Glu Val Val Asp Ile Phe Gln Val Val Lys Ala Leu Arg Lys Ala
225                 230                 235                 240

Arg Pro Gly Met Val Ser Thr Phe Glu Gln Tyr Gln Phe Leu Tyr Asp
                245                 250                 255

Val Ile Ala Ser Thr Tyr Pro Ala Gln Asn Gly Gln Val Lys Lys Asn
                260                 265                 270

Asn

<210> SEQ ID NO 12
<211> LENGTH: 7
<212> TYPE: PRT
<213> ORGANISM: Artificial Sequence
<220> FEATURE:
<223> OTHER INFORMATION: Conserved Protein Sequence

<400> SEQUENCE: 12

Lys Cys Ala Gln Tyr Trp Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Conserved Protein Sequence

<400> SEQUENCE: 13

His Cys Ser Ala Gly Ile Gly
1               5
```